(12) United States Patent
Wildeboer et al.

(10) Patent No.: US 12,369,887 B2
(45) Date of Patent: Jul. 29, 2025

(54) METHOD AND SYSTEM FOR GENERATING A SYNTHETIC ELASTOGRAPHY IMAGE

(71) Applicant: KONINKLIJKE PHILIPS N.V., Eindhoven (NL)

(72) Inventors: Rogier Rudolf Wildeboer, Eindhoven (NL); Ruud Johannes Gerardus van Sloun, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 643 days.

(21) Appl. No.: 17/618,966

(22) PCT Filed: Jun. 10, 2020

(86) PCT No.: PCT/EP2020/066009
§ 371 (c)(1),
(2) Date: Dec. 14, 2021

(87) PCT Pub. No.: WO2020/254159
PCT Pub. Date: Dec. 24, 2020

(65) Prior Publication Data
US 2022/0361848 A1     Nov. 17, 2022

(30) Foreign Application Priority Data
Jun. 20, 2019   (EP) ..................................... 19181415

(51) Int. Cl.
*A61B 8/00*     (2006.01)
(52) U.S. Cl.
CPC ............ *A61B 8/4483* (2013.01); *A61B 8/485* (2013.01); *A61B 8/52* (2013.01)

(58) Field of Classification Search
None
See application file for complete search history.

(56) References Cited

U.S. PATENT DOCUMENTS

| | | |
|---|---|---|
| 2018/0132830 A1 | 5/2018 | Mahmoud et al. |
| 2019/0049540 A1 | 2/2019 | Odry et al. |
| 2019/0183461 A1* | 6/2019 | Sonoyama .......... G01S 7/52042 |

(Continued)

FOREIGN PATENT DOCUMENTS

| | | | |
|---|---|---|---|
| CN | 103815932 A | 5/2014 | |
| JP | 2018029788 A | * 3/2018 | ............... A61B 8/08 |

(Continued)

OTHER PUBLICATIONS

Lee et al. Deep Learning in Ultrasound elastography imaging, Published Oct. 14, 2020 (Year: 2020).*

(Continued)

*Primary Examiner* — Gabriel I Garcia (57) ABSTRACT

The invention relates to a method for generating a synthetic elastography image (18), the method comprising the steps of (a) receiving a B-mode ultrasound image (5) of a region of interest; (b) generating a synthetic elastography image (18) of the region of interest by applying a trained artificial neural network (16) to the B-mode ultrasound image (5). The invention also relates to a method for training an artificial neural network (16)5 useful in generating synthetic elastography images, and a related computer program and system.

14 Claims, 6 Drawing Sheets

(56) References Cited

U.S. PATENT DOCUMENTS

2019/0336108 A1* 11/2019 Hope Simpson ... G01S 15/8915

FOREIGN PATENT DOCUMENTS

| WO | 2018048507 A1 | 3/2018 |
|---|---|---|
| WO | 2018127497 A1 | 7/2018 |

OTHER PUBLICATIONS

International Search Report and Written Opinion for PCT/EP2020/066009; Date of Mailing: Sep. 3, 2020, 13 pages.

Feigin, M. et al., "A Deep Learning Framework For Single-Sided Sound Speed Inversion in Medical Ultrasound", IEEE Trans Biomed Eng. 2018; 10 pages.

Wu, S. et al., "Direct Reconstruction of Ultrasound Elastography using an end-to-end Deep Neural Network", International Conference on Medical Image Computing and Computer Assisted Intervention (MICCAI), 2018, 8 pages.

Tehrani, A.K.Z, et al., Application of Demons algorithm in ultrasound elastography using B-mode ultrasound images, SPIE BiOS, 2019, 8 pages.

Ahmed, T. et al., "Shear-net: An End-to-End Deep Learning Approach for Single Push Ultrasound Shear Wave Elasticity Imaging", Project: Ultrasound Elasticity imaging for early cancer detection, 2019, 12 pages.

Armanious, K. et al., "MedGAN: Medical image translation using GANs", arXiv:1806.06397v2, Jun. 2018, 16 pages.

Yoon, Y.H. et al., "Efficient B-Mode Ultrasound Image Reconstruction From Sub-Sampled RF Data Using Deep Learning", IEEE Transactions on Medical Imaging, 2019, vol. 38, No. 2, 12 pages.

Liu, S. et al., "Deep Learning in Medical Ultrasound Analysis: A Review", Engineering, 2019, vol. 5, pp. 261-275.

Wildeboer, R.R. et al., "Synthetic Elastography using B-mode Ultrasound through a Deep Fully-Convolutional Neural Network", IEEE Trans Ultrason Ferroelectr Freq Control, 2020, 10 pages.

Yang, X. et al., "Tissue elasticity estimation of ultrasonic images based on block matching method," Proceedings of the academic conference of ultrasonic diagnosis and treatment, biological effect, instrument engineering and Chongqing ultrasonic medical engineering society of China ultrasonic medical engineering society, 2012, 9 pages.

* cited by examiner

METHOD AND SYSTEM FOR GENERATING A SYNTHETIC ELASTOGRAPHY IMAGE

CROSS-REFERENCE TO PRIOR APPLICATIONS

This application is the U.S. National Phase application under 35 U.S.C. § 371 of International Application No. PCT/EP2020/066009, filed on Jun. 10, 2020, which claims the benefit of European Patent Application No. 19181415, filed on Jun. 20, 2019. These applications are hereby incorporated by reference herein.

FIELD OF THE INVENTION

The invention relates to a computer-implemented method for generating a synthetic elastography image, a method for training an artificial neural network useful in generating synthetic elastography images from B-mode ultrasound images, to a method for training the artificial neural network or a second artificial neural network to provide a confidence map, and a related computer program and system.

BACKGROUND OF THE INVENTION

Tissue elasticity or stiffness is an important marker in biomedicine, for example in cancer imaging or the assessment of musculoskeletal pathologies. Whether the tissue is hard or soft may provide important diagnostic information. For example, cancerous tumours will often be harder than the surrounding tissue, and liver stiffness is usually indicative of various disease conditions, including cirrhosis and hepatitis. To image the elastic properties of tissue, one needs to record how it behaves when deformed. In ultrasound elastography, usually a radiation force of a focused ultrasound pulse is used to remotely create a "push" inside the tissue. For example, shear-wave elastography (SWE) is an advanced technique that enables local elasticity estimation and the generation of 2D-elastograms. In SWE, a "push" is induced deep in the tissue by a sequence of acoustic radiation force "push" pulses. The disturbance created by this "push" travels sideways (laterally) through the tissue as a shear-wave. By using ultrafast ultrasound imaging to see how fast the shear waves travel to different lateral positions, the stiffness of the intervening tissue is inferred, and an elastography image, also referred to as elastogram, may be generated. However, to assess the shear-wave speed, either a stroboscopic technique or ultrafast imaging using a frame rate in the order of 1000 Hz has to be employed. These recordings have then to be processed to generate 2D-elastographic maps.

SWE images are known to be sensitive to, inter alia, ultrasound probe pressure, motion artefacts and the location of the region of interest (ROI). Moreover, SWE requires special ultrasound (US) transducers having the capability of generating high acoustic radiation force "push" pulses and immediately followed by high-frame-rate imaging. Thus, SWE may not be readily available in many ultrasound equipment, and where it is, it is computationally demanding and has a low frame rate. It would, therefore, be advantageous to have a robust technique to obtain elastography images without requiring sophisticated acquisition schemes or specialized hardware components.

Conventional B-mode ultrasound produces 2D images with fast acquisition and image reconstruction times.

US 2018/0132830 A1 discloses a method for reconstructing displacement and strain maps of human tissue of a subject in vivo. The method includes applying a mechanical deformation to a target area and imaging the tissue while the deformation is applied on the target area, measuring the axial and lateral displacements and strains in the target area to thereby differentiate between tissues of different stiffness and strain responses. Particularly, the document discloses the reconstruction of displacement and strain images from conventional ultrasound B-mode images. Accordingly, the described method requires the application of a mechanical "push", which is done, for example, by the user's hand.

In M. Feigin et al., "A Deep Learning Framework For Single-Sided Sound Speed Inversion in Medical Ultrasound", papers submitted to IEEE, Dec. 10, 2018, an alternative approach to shear-wave imaging is used, which employs single-sided pressure-wave velocity measurements from a conventional ultrasound probe. The method uses the raw ultrasound channel data and produces a corresponding tissue sound speed map using a fully convolutional deep neural network.

OBJECT OF THE INVENTION

It is, therefore, an object of the invention to provide a method (and related computer program and system) to generate elastography images in a faster and less computationally-demanding manner, and which, in addition, does not require specialized ultrasound probes.

SUMMARY OF THE INVENTION

This object is met or exceeded by a computer-implemented method for generating a synthetic elastography image according to claim 1, a method for training an artificial neural network useful in generating synthetic elastography images according to claim 10, a method for training a second artificial neural network useful in providing a confidence map according to claim 12, a computer program according to claim 13 and a system according to claim 14. Advantageous embodiments are set out in the dependent claims. Any features, advantages or alternative embodiments described herein in relation to the claimed method are also applicable to the other claim categories, in particular the claimed system, computer program and vice versa. In particular, the trained artificial neural network(s) can be provided or improved by the claimed training method(s). Furthermore, the input/output data to the trained artificial neural network can comprise advantageous features and embodiments of the input/output training data, and vice versa.

According to a first aspect, the invention provides a method for generating a synthetic elastography image. The method comprises the steps of (a) receiving a B-mode ultrasound image of a region of interest, and (b) generating a synthetic elastography image of the region of interest by applying a trained artificial neural network to the B-mode ultrasound image. Preferably, the method is being executed by a computational unit, wherein a B-mode ultrasound image is received via a first interface. Optionally, the output of the trained artificial neural network (NN), i.e. the synthetic elastography image, is outputted, e.g. via a second interface. The method may further include step of displaying the synthetic elastography image, for example side-by-side or overlaid with the B-mode ultrasound image forming the input to the NN.

Accordingly, the invention provides a method of generating elastograms from a single B-mode image, rather than from the displacement maps estimated from a series of B-mode images tracking a mechanical deformation, or from raw ultrasound channel data (radiofrequency data). Rather, any B-mode image can serve as input for the trained artificial neural network (NN) of the invention. Unlike prior art methods, the invention does not calculate displacements to estimate elasticity, but generates elastograms based on the special B-mode characteristics. The invention has recognized that, although B-mode ultrasound measures tissue echogenicity rather than elasticity, also B-mode ultrasound images may carry texture information that are linked to the underlying tissue structure and mechanical properties. The NN is trained to recognize this and transform that information into an elasticity map (a synthetic elastography image), which is at least similar to the elastography images that may currently be produced with ultrasound-elastography techniques, such as shear-wave elastography protocols. Accordingly, the invention provides a deep learning solution that enables robust synthesis of SWE-like images from simple, conventional B-mode acquisitions.

The invention therefore allows to generate synthetic elastography images at the frame rate of B-mode ultrasound. Thus, the invention may be used to append or replace shear-wave elastography in conventional scanners, alleviating the heavy system requirements and the operator-sensitivities still exhibited by conventional ultrasound elastography techniques, such as SWE. Moreover, the method of the invention could be performed by ultrasound scanners that are not sufficiently equipped for SWE itself. Another application could be retrospective elastography, in which synthetic elastography images are generated from B-mode images that have already been recorded. This is could be used for additional tissue typing in a later stage of the diagnostic process.

The computational unit executing the method may be any data-processing unit, such as a GPU (graphics processing unit), CPU (central processing unit) or other digital data processing equipment. Preferably, the method may be executed by a computational unit which is part of or connected to an ultrasound scanner used in diagnostic imaging. In useful embodiments the output of the NN, namely the synthetic elasticity image, is outputted via an interface of the computational unit and may be displayed to a user, for example on a computer screen, screen of a mobile device, television set or other display device. The method may also comprise a step of acquiring a B-mode ultrasound image of the region of interest; however, such B-mode image may also be provided from a data storage, either locally or remotely. Because the inventive method is very fast, it may be executed in real-time, immediately after acquisition of the B-mode ultrasound image, to thereby allow a direct assessment of the elastography image. The B-mode ultrasound image may be any image in brightness mode, i.e. in which the intensity of an ultrasound echo is depicted as brightness. It may be acquired by any known means.

The B-mode ultrasound image is preferably a two-dimensional (2D) image, for example represented by a 2D-matrix of grayscale values. The method may also be applied to a stack of 2D images, which together cover a volume of interest. However, the method is also applicable three-dimensional (3D) B-mode ultrasound images, or even to one-dimensional (1D) images. The B-mode ultrasound image may be provided in any format, for example, in DICOM (Digital Imaging and Communications in Medicine) standard.

An artificial neural network (NN) is based on a collection of connected artificial neurons, also called nodes, wherein each connection (also called edge) can transmit a signal from one node to another. Each artificial neuron receiving a signal may process it and transfer it to further artificial neurons connected to it. In useful embodiments, the artificial neurons of the inventive NN are arranged in layers. The input signals, i.e. the pixel values of the B-mode ultrasound image, travel from the first layer, also termed the input layer, to the last layer, the output layer. In useful embodiments, the NN is a feed-forward network. The neural network preferably comprises several layers, including hidden layers, and is thus, preferably, a deep network.

In an embodiment, the NN is trained on the basis of machine learning techniques, in particular deep learning, for example by back propagation. The training data used may be elastography images generated by any elastography technique, preferably an ultrasound elastography technique. The synthetic elastography images generated by the NN will be similar to the images generated by the ultrasound elastographic technique used as output training data.

In a preferred embodiment, the NN will be trained on SWE, however other ultrasound elastography images may also be used in the training. For example, the NN may be trained on quasi-static elastography images. In this technique, an external compression is applied to the tissue, and the ultrasound images before and after the compression are compared. The areas of the image that are least deformed are the ones that are stiffest, while the most deformed areas are the least stiff. The elastography image is an image of the relative distortions (strains). The NN may also be trained on acoustic radiation force impulse images (ARFI). This technique uses an acoustic radiation force from a focused ultrasound beam to create a "push" inside the tissue. The amount the tissue along the axis of the beam is pushed down reflects tissue's stiffness. By pushing in many different places, a map of the tissues stiffness is built up. The NN may also be trained on elastography images obtained by supersonic shear imaging (SSI), which is based on SWE: The technique uses acoustic radiation force to induce a "push" inside the tissue of interest, and the tissues stiffness is computed from how fast the resulting shear-wave travels through the tissue. Local tissue velocity maps are obtained with a special tracking technique and provide a full movie of the shear-wave propagation though the tissue.

In further embodiments, the NN of the invention may also be trained on magnetic resonance elastography images (MRE). In MRE, a mechanical vibrator is used on the surface of the patient's body, and an imaging acquisition sequence measuring velocity of the shear-waves travelling into the patient's deeper tissues is used to infer the tissue's stiffness.

Whatever the training data used, the synthetic elastography images are abbreviated herein to sSWE images.

The trained artificial neural network(s) according to the invention may be provided in the form of a software program, but may also be implemented as hardware. Further, the trained NN may be provided in the form of a trained function, which is not necessarily structured exactly the same way as the neural network which was trained. For example, if certain connections/edges have the weight 0 after training, such connections may be omitted when providing a trained function, which is based on the trained NN.

The synthetic elastography images generated by the inventive NN proved to bear a high correlation with SWE images obtained by shear-wave elastography imaging. Thus, the inventive method allows to obtain synthetic elastography images without requiring this specialized hardware and with less computational effort than in conventional shear-wave elastography imaging. As no ultrafast imaging schemes, no acoustic radiation force "push" pulses and no advanced sequences to produce 2D-elastograms are needed, the generation of the synthetic elastography images (sSWE) is much faster and less computationally demanding than SWE itself, and can be carried out with a conventional ultrasound probe, which is adapted for B-mode ultrasound imaging, but not for SWE. The method of the invention does not require a specialized ultrasound probe. The synthetic elastography images generated by the inventive NN may be used for diagnostic purposes. They carry diagnostic information in the form of elasticity values.

According to an embodiment, the input to the trained artificial neural network, namely B-mode ultrasound image, has the same size and dimensions as the output of the trained NN, namely the synthetic elastography image. In this context, size means the size of the matrix of data points, and the dimensionality of the input, e.g. 2D or 3D. In other words, preferably the trained NN serves as an end-to-end mapping function that transforms the B-mode image to an elastography-like image of the same size and dimensions. Preferably, the input to the NN will be a two-dimensional or a stack of two-dimensional B-mode images, and also the output will be a two-dimensional or stack of two-dimensional elastography images of the same size.

According to a preferred embodiment, the trained NN comprises at least one convolutional layer. A convolutional layer applies a relatively small filter kernel over the entire input layer, so that the neurons inside the layer are connected to only a small region of the layer before it. This architecture ensures that the learned filter kernels produce the strongest response to a spatially local input pattern. Each filter kernel is replicated across the entire input layer. In useful embodiments of the invention, the convolutional layer's parameters comprise a set of learnable filter kernels, which have a small receptive field, but which may extend through the full depth of the input volume. During a forward pass through the convolutional layer, each filter kernel is convolved across the width and height of the input volume, computing the dot product between the entries of the filter kernel and the input, and producing a feature map of that filter. Stacking the feature maps for all filter kernels along the depth dimension forms the full output volume of the convolutional layer. Every entry in the output layer, which comprises several feature maps or combinations of feature maps, can thus be interpreted as an output of a neuron that looks at a small region in the input and shares parameters with neurons in the same feature map.

According to a preferred embodiment, the trained artificial neural network is a deep fully-convolutional neural network. In this regard, fully-convolutional means that there are no fully-connected layers. Rather, the inventive NN exploits spatially local correlation by enforcing a sparse local connectivity pattern between neurons of adjacent layers: Each neuron is connected to only a small region of the input volume. A deep convolutional neural network comprises at least two convolutional layers. In fact, the trained NN of the invention preferably comprises at least four convolutional layers, more preferred eight or more convolutional layers. A further advantage of a fully-convolutional neural network is that the trained NN can be applied to input images of any size: Since the filter kernels are replicated across the entire input or preceding layer, a convolutional network may be applied to images of any size. It is preferred that the input to the NN is two-dimensional, as this will lead to significantly less training parameters in the NN.

In useful embodiment, the convolutional layer or layers of the NN comprise convolutional filter kernels having a size of 3×3 pixels, less preferred 2×2 or 4×4 pixels, in the case of a 2D-input image. In the case of a 3D-input image, also the filter kernels will be 3D, for example, 3×3×3 or 2×2×2-pixels.

In useful embodiments, the depth of each convolutional layer is between 8 and 64, preferably 16-32, most preferred 32, meaning that 32 different feature maps, produced by different filter kernels are part of each convolutional layer. If two convolutional layers follow one another, preferably their depth remains the same, wherein each of the 32 feature maps of the subsequent layer are produced by adding together the result of convoluting each of the feature maps of the previous layer with a separately trained filter kernel. Accordingly, a deep convolutional layer having a depth of 32, and connected to a subsequent layer having a depth of 32, requires 32×32 filter kernels to train.

According to a further useful embodiment, the trained artificial neural network comprises at least one unit comprising 1-3, preferably 2-3, most preferred 2 convolutional layers followed by a pooling layer or an up-sampling layer. For example, every two convolutional layers are followed by a pooling (down-sampling) operation, preferably a 2×2 max-pooling operation, which reduces a kernel of four pixels to one by projecting only the highest value onto the subsequent layer, which, thus, has a smaller size. This is a step that forces the network to learn larger-scale features that are less sensitive to local variations. This may be performed in a first part of the NN, referred to as the encoder part. In some embodiments, there will be a second part of the network, referred to as the decoder part, in which the max-pooling operations are replaced by e.g. nearest-neighbour up-sampling, so as to increase the size of the layers again, so that the output layer has the same size as the input layer.

In an embodiment, the trained artificial neural network comprises an encoder-decoder architecture. Preferably, the NN comprises exactly one encoder part and exactly one decoder part. Accordingly, the size of the layers (e.g. the number of pixels processed therein) is gradually reduced as one progresses deeper into the network. The central layers are termed deep latent space. In useful embodiments, the layer or layers in the deep latent space are reduced in size in each dimension by a factor of 4-16, e.g. 8 with regard to the input layer. The deep latent space may also comprise at least one convolutional layer. For example, it may consist of two convolutional layers.

According to an embodiment, the NN comprises an encoder part, comprising at least one, preferably a plurality of pooling or down-sampling layers. The encoder part of the NN is followed by a decoder part, which comprises at least one, preferably a plurality of up-sampling layers. Preferably, the NN comprises exactly one encoder part comprising a plurality of pooling or down-sampling layers, and exactly one decoder part comprising a plurality of up-sampling layers. Optionally, the deep latent space between decoder part and encoder part comprises further layers, in particular it may comprises two convolutional layers. The pooling layers may be max-pooling layers, but may also use other functions, such as average pooling or 12-norm pooling. The up-sampling layers may use nearest-neighbour up-sampling, but may also use linear interpolation. Preferably, the decoder part is a mirrored version of the encoder part, wherein the down-sampling layers are replaced by up-sampling layers. Preferably, the encoder part comprises at least two, preferably three max-pooling layers having a filter kernel of 2×2 and a stride of 2. When the stride is 2, the filter kernel moves 2 pixels at a time as it slides around the layer. Thereby, from each 2×2 square of neurons of the preceding convolutional layer, only the activity of the most active (i.e. highest value) neuron is used for the further calculations. Thereby, the receptive field in the deeper layers grows automatically, without having to reduce the size of the filter kernels. Further, it is possible to build deeper networks, allowing more complex operations.

According to an embodiment, the trained artificial neural network comprises a layer or layers between the decoder part and the encoder part. The layer or layers between decoder part and encoder part are termed deep latent space. Optionally, there may be operations performed in deep latent space as well. The deep latent space may comprise at least one convolutional layer. According to one embodiment, the deep latent space comprises or consists of two convolutional layers as well. According to another embodiment, the deep latent space comprises at least one fully-connected layer. In a preferred embodiment, the encoding part of the network consists in total of 6 convolutional and 3 max-pooling layers mapping the input images into the deep latent space. Preferably, also the decoder part of the network may comprise or consist of in total of 6 convolutional and 3 up-sampling layers.

According to an embodiment, the NN comprises an encoder part comprising a plurality of convolutional layers, wherein each one to three, preferably two to three, most preferred two convolutional layers are followed by a pooling layer, and a decoder part comprising a plurality of convolutional layers, wherein each one to three, preferably two to three, most preferred two convolutional layers are followed by an up-sampling layers. The convolutional layers in the decoder part preferably have the same filter kernel size and stride than in the encoder part, for example filter kernels of 3×3×3 for a 3D input image and 2×2 for a 2D input image. The operation performed by the convolutional layers on the decoder part may be described as a de-convolution.

Preferably, each two convolutional layers are followed by a pooling layer or up-sampling layer in the encoder and decoder parts, respectively. In an embodiment, the encoder part comprises two to four, preferably three, such units made up of one to three convolutional layers followed by pooling layer. Since the decoder part is a mirrored version of the encoder, preferably also the decoder part, comprises two to four, preferably three, units consisting of one to three convolutional layers followed by an up-sampling layer.

According to a further embodiment, the NN comprises at least one skip connection from a layer in the encoder part to an equally-sized layer in the decoder part. In other words, the NN is preferably equipped with direct "skip" connections from the at least one encoder filter layer to its equally-sized decoder counterpart. By transferring the encoder layer output across the latent space and concatenating it to the larger-scale model features during decoding, the NN is enabled to optimally combine fine and coarse level information and generate higher-resolution elastography image estimations. In useful embodiments, there is one skip connection from each unit comprising one to three convolutional layers followed by a pooling layer in the encoder part to the corresponding unit comprising one to three convolutional layers followed by an up-sampling layer in the encoder part. The skip connection may be implemented by adding or concatenating the output of the respective layer on the encoder part to the output of the corresponding layer in the decoder part. For example, if the convolutional layers have a depth of 32 in the encoder part, they will be concatenated to the 32 feature maps in the corresponding layer in the decoder part, so that there will be 64 feature maps. By using twice the number of filter kernels (e.g. 64×32) in the convolutional layer in the decoder part, these 64 feature maps will get mapped back to 32 feature maps in the subsequent layer. Thereby, each feature map of the following convolutional layers in the decoder part may be influenced by the input provided by the skip connection from the encoder part.

The stride, with which the filter kernels are applied is preferably 1, i.e. filter kernels are moved one pixel at a time. This leads to overlapping receptive fields between the columns, and the grid size is not reduced between convolutional layers. Alternatively, the stride may be 2, such that the filter kernel jumps 2 pixels at a time as they slide around. Thereby, the size of the subsequent layer is reduced by a factor of 2 in each dimension, for example by 2×2 in a two-dimensional grid. Thereby, the convolutional network may be constructed without the need for down-sampling layers.

In most embodiments of the invention, the NN comprises at least one layer including an activation function, preferably a non-liner activation function. For example, the results of each convolutional layer may be passed through a non-linear activation function. Preferably, such activation function propagates both positive and negative input values with unbounded output values. By "unbounded" it is meant that the output value of the activation function is not limited to any particular value (such as +1 or −1). Preferably, any value may in principle be obtained, thereby preserving the dynamic range of the input data. Preferably, the activation function of the invention introduces non-linearity while preserving negative signal components, in order to minimize the risk of vanishing gradients during training. In useful embodiments, the activation function used in the convolutional layers is the leaky rectifier linear unit (LReLU), which may be described as follows:

$$f(x) = \begin{cases} x & \text{if } x > 0 \\ \alpha x & \text{otherwise} \end{cases}$$

with an α-value of between 0.01 and 0.4, for example 0.1. Alternatively, a hyperbolic tangent activation may be used in order to preserve negative values. In other embodiments, the activation function is a Rectified Linear Unit (ReLU), hyperbolic tangent, or sigmoid function. In a further embodiment, the activation function may be an antirectifier function, which combines a sample-wise L2 normalization with two rectifier linear units (ReLU) activations, thereby concatenating the positive and negative part of the input. Preferably, the results of each convolutional layer is passed through such non-linear activation function.

According to another embodiment of the invention, the latent space includes a domain adaptation structure or function, which enables a transfer of sSWE generation to other ultrasound machines and acquisitions, e.g. to other types of ultrasound scanners and/or to other elastographic acquisition techniques than those with which the network was trained. This may, for example, be done by applying a factor and/or shift and/or other function to each node in latent space. Accordingly, at least one layer in latent space, i.e. the layer(s) of smallest size between encoder and decoder part of the network, may comprise a domain adaptation function, which aligns the feature maps to a different system. For example, if the NN has been trained on SWE images, it may yet be applied to supersonic elastography imaging by shifting and/or scaling the nodes in latent space, e.g. by adding a layer which applies such adaptation function to each node. This may correspond to a translation applied to the layer in latent space. The translation and scaling required may be established by comparing the encoded latent spaces of two datasets of different domains. In a preferred embodiment, the mean and variance of the latent vectors are corrected.

According to another aspect, the invention provides a method for training an artificial neural network useful in generating synthetic elastography images from B-mode ultrasound images, the method comprising:
(a) Receiving input training data, namely at least one B-mode ultrasound image of a region of interest, wherein the B-mode ultrasound image has been acquired during an ultrasound examination of a human or animal subject;
(b) Receiving output training data, namely at least one ultrasound elastography image of the region of interest acquired by means of an ultrasound elastography technique during the same ultrasound examination;
(c) training the artificial neural network by using the input training data and the output training data.

The training method may be used to train the artificial neural network capable of generating a synthetic elastography image of the region of interest described herein. It is trained on B-mode ultrasound images as input training data, and an elastography image of the same region of interest acquired by means of any ultrasound elastography technique during the same ultrasound examination, or concurrently to the B-mode ultrasound image. The elastography image may be a shear-wave elastography (SWE) image, but may also be acquired using any other ultrasound elastography technique. For example, it may be acquired by quasi-static elastography imaging, acoustic radiation force impulse imaging (ARFI), supersonic shear imaging (SSI) or transient elastography or possibly even by magnetic resonance elastography (MRE). Depending on the training data used, the appearance of the output of the NN will be different, as the inventive method is mainly data-driven.

The training method described herein may be used to provide the artificial neural network useful in generating synthetic elastography images, i.e. initially train the NN. It may also be used to recalibrate an already trained network. Accordingly, it is possible to implement a combined SWE/sSWE scheme that performs real-time full-view synthetic shear-wave elastography imaging (by using the method of claim 1 and B-mode images as input), but occasionally calibrates the model with conventional elastography images, in particular conventional SWE images, during scanning.

According to an alternative method of calibrating the artificial neural network configured to generate synthetic elastography images from B-mode ultrasound images, the method comprises the additional steps of:
obtaining at least one (conventional) ultrasound elastography image of the region of interest, acquired by means of ultrasound elastography technique during the same ultrasound examination as the B-mode ultrasound image;
recalibrating the trained artificial neural network based on the elastography image and the synthetic elastography image.

In an embodiment, the method further comprises the step of estimating a confidence map for the synthetic elastography image (sSWE). Accordingly, the method comprises a further step of applying the NN or a second trained artificial neural network to the B-mode ultrasound image, wherein the output of the NN or the second trained artificial neural network is a confidence map comprising a plurality of confidence scores, each confidence score being representative of the confidence level of the value of the corresponding pixel of the synthetic elastography image; and optionally a further step of providing and/or displaying the confidence map. Accordingly, this step allows the concurrent estimation of SWE confidence, which is then used to identify low-confidence regions due to shear-wave artefacts such as signal voids in (pseudo) liquid lesions or B-mode artefacts such as shadowing or reverberation. The method may further include step of displaying the confidence map, for example side-by-side or overlaid with the sSWE.

The NN or the second NN is preferably trained for providing the confidence map in a method comprising the following steps:
a) Receiving input training data, namely at least one synthetic elastography image generated by the method described herein, wherein the B-mode ultrasound image used to generate the synthetic elastography image has been acquired during an ultrasound examination of a human or animal subject;
(b) Receiving output training data, namely at least one ultrasound elastography image of the region of interest acquired by means of an ultrasound elastography technique during the same ultrasound examination;
(c) Training the artificial neural network by using the input training data and the output training data.

In an embodiment, the confidence map comprises not only the confidence of the NN or second NN in predicting SWE, but also the intrinsic confidence of SWE acquisition itself (which is usually estimated during the SWE protocol based on fitting, noise, etc.). Also this confidence could be trained in an embodiment of the above training method. Preferably, both the sSWE image and the corresponding confidence map are generated by the same artificial NN, with a B-mode image as input. Alternatively, the confidence map may be provided with a second NN, which may have the same architecture as the (first) NN useful in generating elastography images of the region of the interest. Alternatively, the second NN may have a simpler architecture, for example it may be a deep convolutional neural network, but it may have fewer layers than the first NN. For example, the second NN may have an encoder-decoder architecture having one or two units comprising one to three convolutional layers followed by a pooling or up-sampling layer on each of the encoder part and the decoder part.

The training of the first and second neural networks may be done by back propagation. In this method, the input training data is propagated through the NN using predetermined filter kernels. The output is compared to the output training data using an error or cost function, the output of which is propagated back through the NN, thereby calculating gradients to find the filter kernels (and possibly other parameters such as bias) that yield minimum errors. This may be done by adjusting the weights of the filter kernels and following negative gradients in the cost function.

In useful embodiments, the neural network uses drop-out layers during training. Therein, certain nodes or filter kernels in the drop-out layer are randomly selected and the values/weights are set to 0. For example, a drop-out layer may have a pre-determined percentage of drop-out nodes such as 30-80%, preferably 40-60%, of all nodes are drop-out and their values/weights set to 0. For the next back propagation of training data, a different set of nodes in the drop-out layer is set to 0. This creates noise during training, but has the advantage that the training converges to a useful minimum. Accordingly, the NN is better trainable. In useful embodiments, each two or three convolutional layers are followed by drop-out layer during training.

The invention is also related to a computer program comprising instructions which, when the program is executed by a computational unit, causes the computational unit to carry out the inventive method. This is true for the method for generating a synthetic elastography image, the additional method steps of applying a second trained artificial neural network to provide a confidence map comprising a plurality of confidence scores, and for the training methods of the first and second artificial neural networks. Alternatively, the neural networks may be implemented as hardware, for example with fixed connections on a chip or other processing unit. The computational unit, which may execute the inventive method, may be any processing unit such as CPU (Central Processing Unit) or GPU (Graphics Processing Unit). The computational unit may be part of a computer, a cloud, a server, a mobile device such as a laptop, tablet computer, mobile phone, smartphone etc. In particular, the computational unit may be part of an ultrasound imaging system. Said ultrasound imaging system may also comprise a display device such as a computer screen.

The invention is also directed to a computer-readable medium comprising instructions which, when executed by a computational unit, causes the computational unit to carry out the method according to the invention, in particular, the method according to any one of claims 1-9 or the training method. Such computer-readable medium may be any digital storage medium, for example a hard disk, a server, a cloud, or a computer, an optical or a magnetic digital storage medium, a CD-ROM, a SSD-card, a SD-card, a DVD or an USB or other memory stick.

According to another aspect, the invention is also related to a system for generating a synthetic elastography image, the system comprising:
a) a first interface, configured for receiving a B-mode ultrasound image of a region of interest;
b) a computational unit configured for applying a trained artificial neural network to the B-mode ultrasound image to thereby generate a synthetic elastography image of the region of interest;
c) a second interface, configured for outputting the synthetic elastography image of the region of interest.

The system is preferably configured to execute the invention for generating a synthetic elastography image. Such a system may be implemented on an ultrasound imaging system, e.g. it is implemented on one of its processing units such as a GPU. However, it is also considerable that the B-mode ultrasound images acquired by the ultrasound imaging system are transferred to another computational unit, local or remote, for example via internet, and the synthetic elastography images of the region of interest are transferred back from there to the ultrasound imaging system and displayed. The second interface may thus be connected to a display device, such as a computer screen, touch screen etc.

Further, the invention is also directed to a system for training a first or second artificial neural network by the training method described herein.

According to a further aspect, the invention is directed to an ultrasound imaging system comprising an ultrasound transducer configured to transmit and receive ultrasound signals; a computational unit configured to generate B-mode ultrasound images from the received ultrasound signals; and wherein the computational unit is also configured to perform the method according to any of claims 1-9. Due to the low computational cost of said method, such a computational unit can be integrated into existing ultrasound systems.

SHORT DESCRIPTION OF THE FIGURES

Useful embodiments of the invention shall now be described with reference to the attached figures. Similar elements or features are designated with the same reference signs in the figures. In the figures.

DESCRIPTION OF EMBODIMENTS

Figure 1:
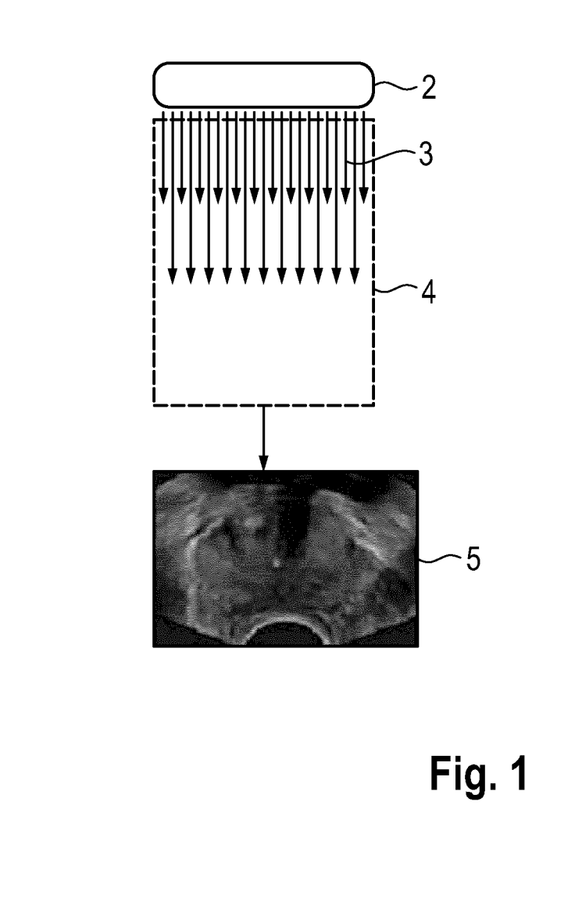
FIG. 1 is a schematic illustration of conventional B-mode ultrasound imaging.

FIG. 1 schematically depicts the process of B-mode ultrasound: An ultrasound probe 2, usually comprising an array of ultrasound transducers, transmits a series of ultrasound pulses 3, for example as compressive wave fronts, into a region of interest 4, usually within a human or animal body. By recording the echoes and performing suitable signal processing such as beam-forming, a B-mode ultrasound image 5 of the region of interest is acquired. This can be done with a high frame rate, especially for 2D images.

Figure 2:
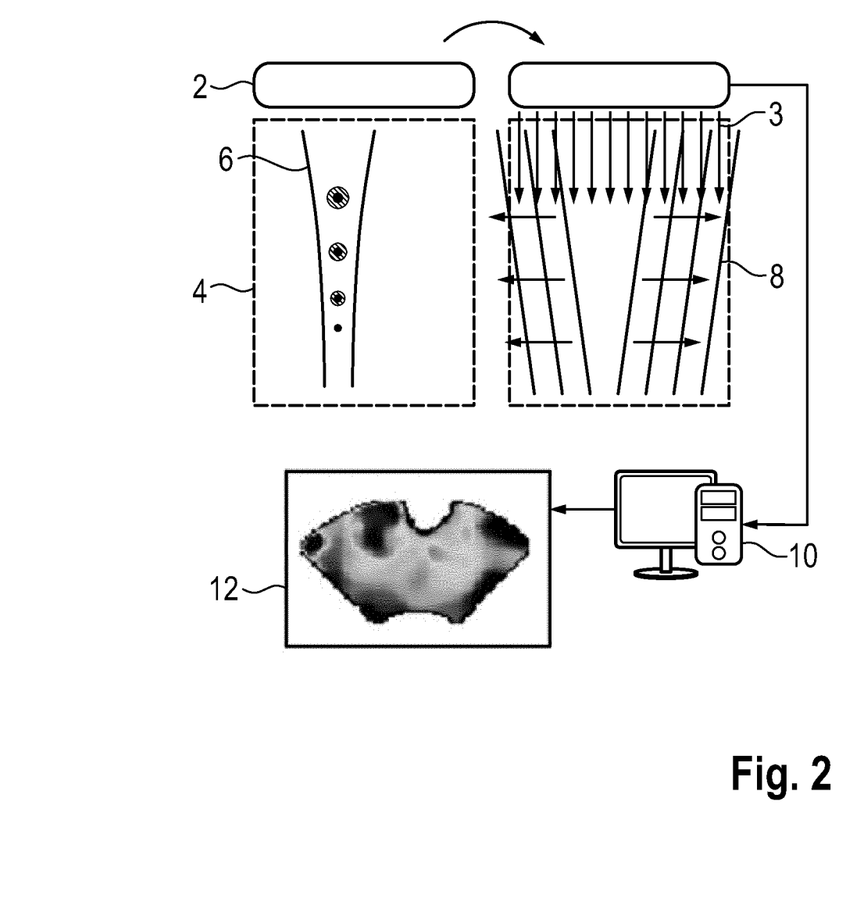
FIG. 2 is a schematic illustration of conventional shear-wave elastography.

FIG. 2 illustrates conventional SWE imaging. An ultrasound probe 2 generates a sequence of acoustic radiation force "push" pulses 6 into the region of interest 4. The "push" pulse results in laterally travelling shear-waves 8, which are recorded by ultrafast imaging by the ultrasound probe 2 and using further ultrasound transmission pulses 3. The recorded echoes are transferred to a computational unit 10, which processes the ultrafast imaging recordings and generates a 2D SWE image 12. The B-mode image 5 and SWE 12 shown in FIGS. 1 and 2 have been acquired from the same region of interest, here during a prostate examination of a human subject.

Figure 3:
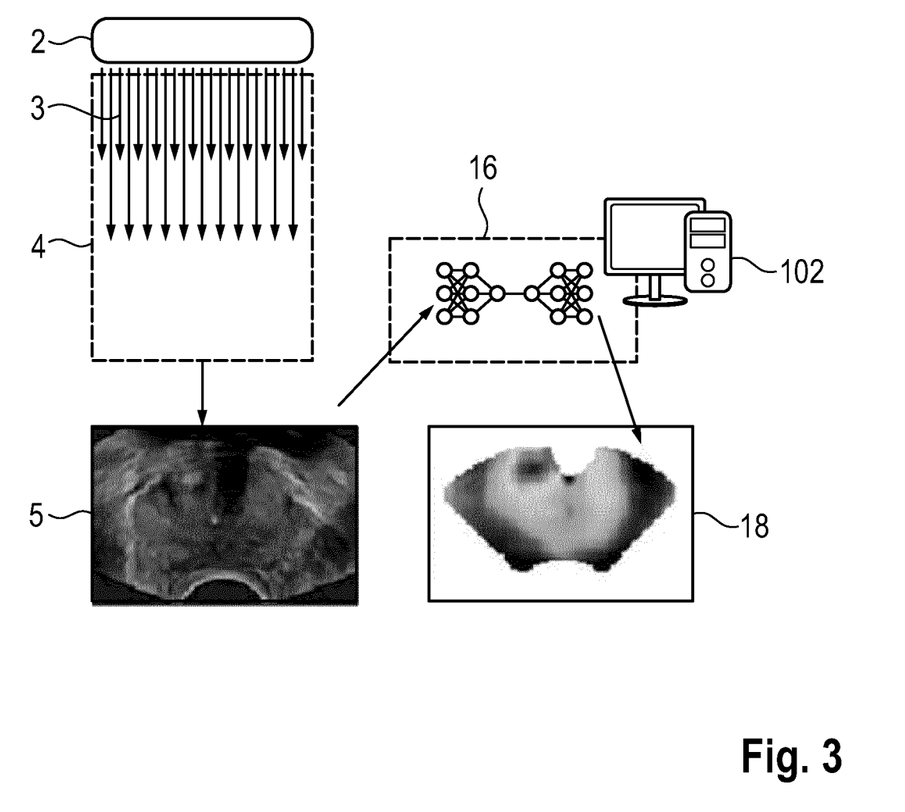
FIG. 3 is a schematic illustration of a method for generating sSWE images according to an embodiment of the invention.

FIG. 3 is a schematic illustration of a method for generating a synthetic SWE image according to an embodiment of the invention: First, a B-mode image 5 is generated in a conventional manner, as illustrated in FIG. 1. The B-mode image 5 is propagated through a trained artificial neural network 16 according to an embodiment of the invention, which is implemented (by software or hardware) on a computational unit 102, which may be the computational unit of a commercial ultrasound scanner. The result is a synthetic elastography image (sSWE) 18, which preferably has the same size and dimensions as the B-mode image—however, it may also have a somewhat coarser grid, as this is also the case in conventional SWE images.

Figure 4:
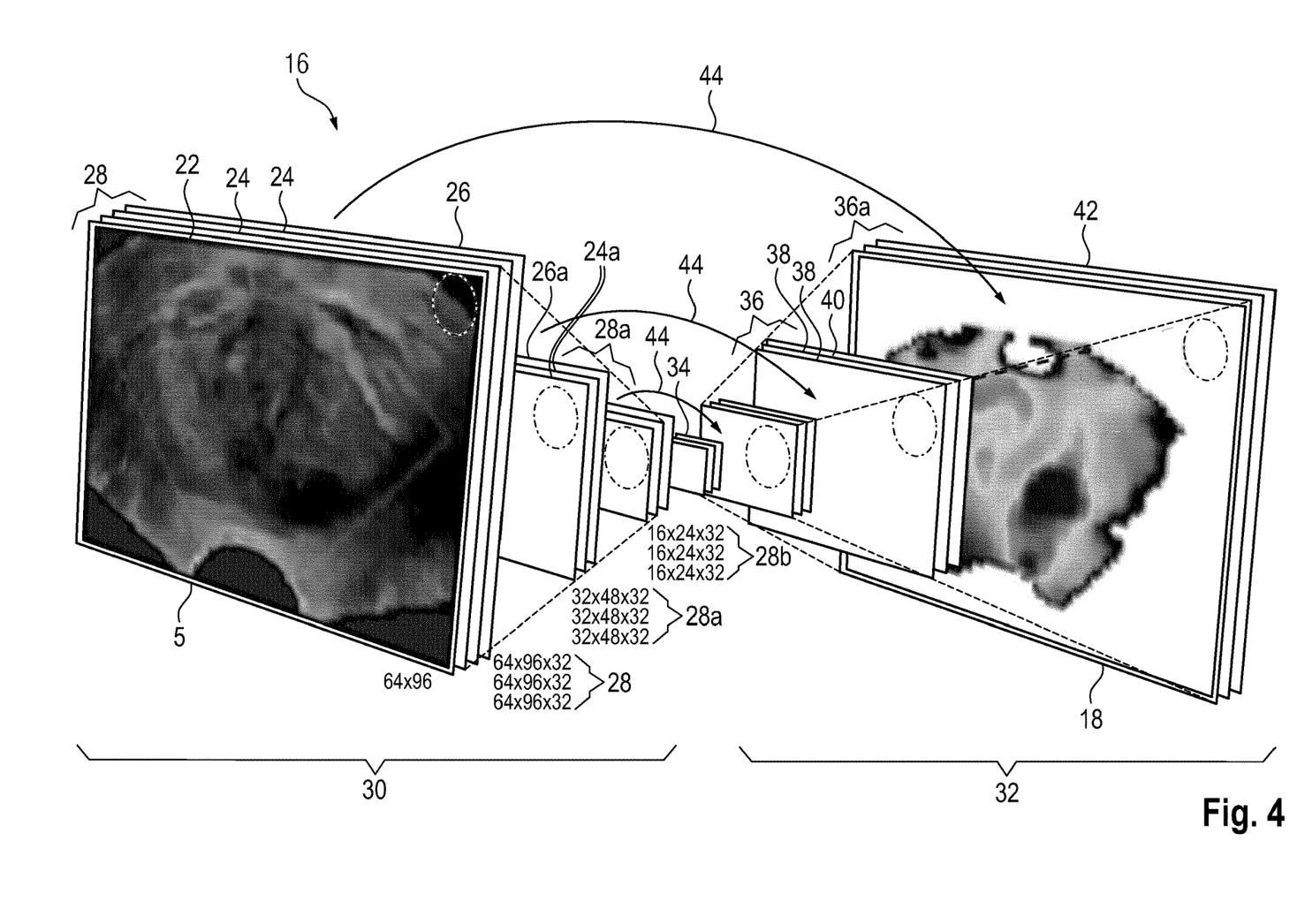
FIG. 4 is a schematic overview of a deep convolutional neural network according to an embodiment of the invention.

FIG. 4 illustrates an embodiment of the NN 16 according to the invention. The input images is forward-propagated through the NN 16 from left to right. The pixel size of the layers is noted to the rights of the respective layer.

A 2D B-mode image 5, in this case having an image size of 64×96 pixels, is fed into the input layer 22. The input layer 22 is followed by two convolutional layers 24 having a depth of 32. Thus, 32 filter kernels are applied to the input layer 22, resulting in 32 feature maps, which form part of each convolutional layer 24. In preferred embodiments, the convolutional layers 24, 24a, 38 of the network each comprise 32 or 32×32 two-dimensional 3×3-pixel convolutional filter kernels, of which the results are passed through a non-linear activation function, in particular a leaky rectified linear unit. The first two convolutional layers 24 in the encoder part 30 are followed by a 2×2 max-pooling layer 26, which reduces a kernel of four pixels to one by projecting only the highest value onto the corresponding node in the following layer, which is again a convolutional layer 24a. The two convolutional layers 24 and the max-pooling layer 26 together form a unit 28. The architecture of this unit is repeated in the following unit 28a comprising two convolutional layers 24a and a max-pooling 26a. From the pixel size of the layers, one can see that the size from each unit 28 to the next unit 28a is reduced by a factor of 2×2. However, the depth (i.e. the number of feature maps comprised in each convolutional layer) stays the same at 32. In this embodiment, there is a total of 3 units 28, 28a and 28b in the encoding part 30 of the network. The pooling layer of the third unit 28b is followed by several layers in deep latent space 34, where the grid/layers have a size of only 8×12×32 or 8×12×64. In this embodiment, the deep latent space consists of two convolutional layers, followed by an up-sampling layer. In another embodiment, one may also count the unit 34 as part of the decoding part 32 of the network. Each unit 36 in the decoder part comprises two convolutional layers 38 followed by an up-sampling layer 40, which projects each pixel/node in the preceding layer onto 2×2 pixels in the following layer by nearest-neighbour up-sampling. Thus, the decoder part 32 is a mirrored version of the encoder part, and comprises 3 units 36, each consisting of two convolutional layers followed by an up-sampling layer, or, in case of the final unit 36a, by an output activation layer 42. The output of the NN is a synthetic shear-wave elastography image 18.

In addition, the deep convolutional neural network (DCNN) 16 is equipped with direct "skip" connections 44 from the encoder filter layer to its equally-sized decoder counterpart. In useful embodiments, there is one skip connection from each unit 28, 28a, 28b in the encoder part 30 to a layer of equal size in the decoder part 32.

Figure 5:
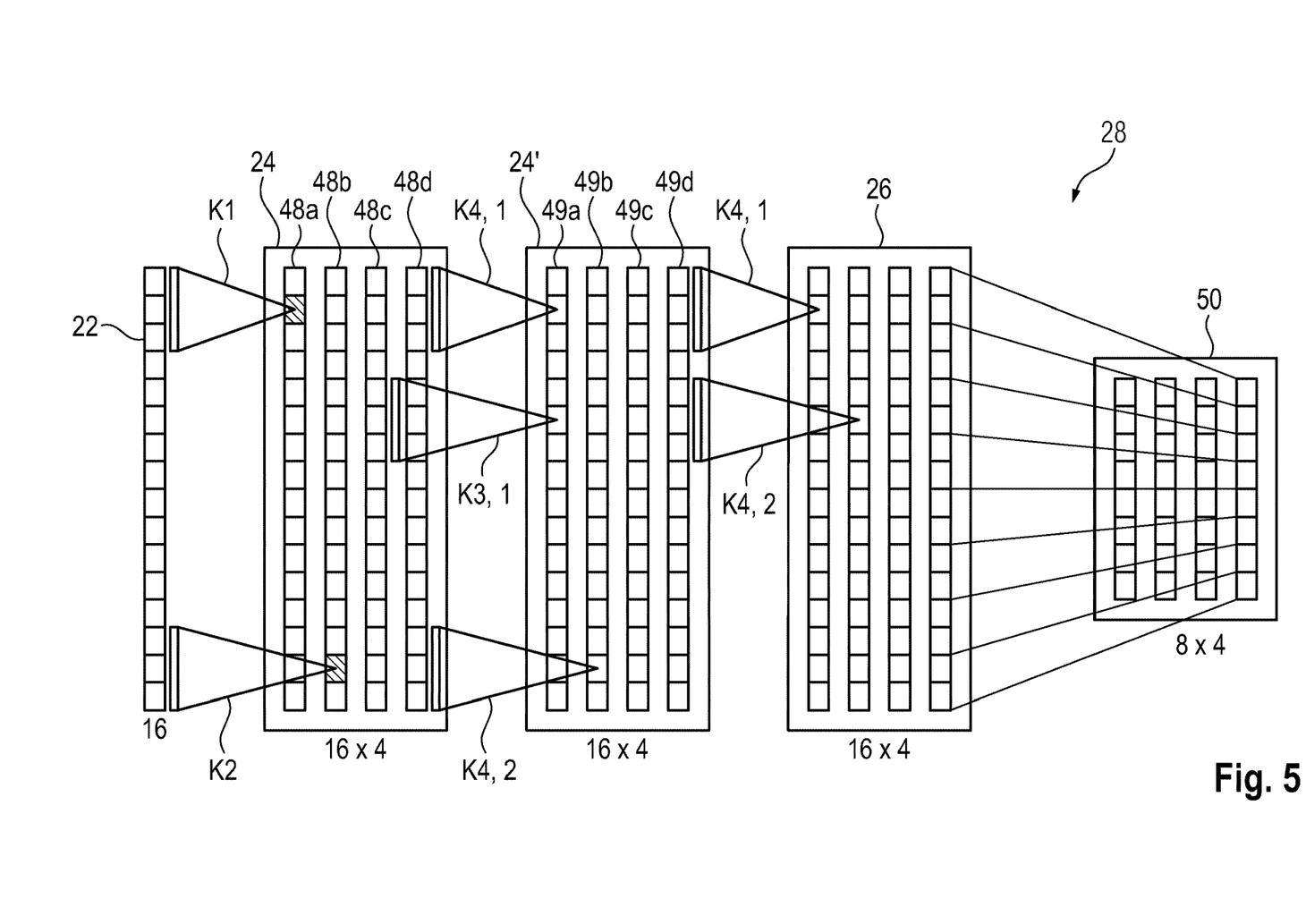
FIG. 5 is a more detailed schematic representation of a unit of the NN according to an embodiment of the invention comprising two convolutional layers and a pooling layer.

FIG. 5 depicts in more detail the unit 28, i.e. the first unit of the encoding part 30 of the network 16. Accordingly, the B-mode image 5 is represented here by a one-dimensional matrix fed into the input layer 22, and comprising 16 pixels, as an illustrative example. The input layer 22 is already a convolutional layer applying four different filter kernels K1, K2 as well as K3 and K4 (not shown), each filter kernel having a size of 3 pixels, to the input data 22. Accordingly, this results in a next layer 24 having a depth of 4, i.e. comprising four feature maps 48a-48d, wherein each feature map activates when it detects some specific type of feature at the corresponding spatial position in the input layer 22. The next convolutional layer 24' involves not four, but 16 filter kernels, wherein each filter kernel sweeps across one feature map in layer 24 and adds the results to one of the four feature maps in layer 24'. For example, the filter kernel K4,1 sweeps over the fourth feature map 48d of layer 24 and adds the result to the first feature map 49a of layer 24'. Filter kernel K3,1 convolves the third feature map 48c of layer 24 and adds it to the first feature map 49a in layer 24'. Thus, 4×4=16 filter kernels are being trained during the training step. Layer 24' is again a fully convolutional layer, resulting in an output having a depth of 4, i.e. comprising four feature maps. This output is fed into a pooling layer 26, which reduces each kernel of 2 pixels to 1 by projecting only the highest value onto the smaller grid, which is here denominated 50. In the framework of the NN, layer 50 may either be already in latent space, or it may be the first convolutional layer of the next unit 28.

An embodiment of the invention was tested as follows: Fifty patients diagnosed with prostate cancer underwent a transrectal SWE examination at the Martini Clinic, University Hospital Hamburg-Eppendorf, Germany. An Aixplorer™ (SuperSonic Imagine, Aixen-Provence, France) equipped with an SE12-3 ultrasound probe was used. For each patient, SWE images were obtained in the basal, mid, and apical section of the prostate. Regions of interest were chosen such that they covered the entire prostate or parts of the prostate. Allocating the first 40 patients in the training set, a fully-convolutional deep neural network was trained to synthesize an SWE image given the corresponding B-mode (side-by-side-view) image. Data augmentation was leveraged to mitigate the risk of overfitting and prevent artefacts hampering the training by only estimating loss gradients from high-confidence SWE measurements. The method was tested on 30 image planes from the remaining 10 patients.

Figure 6:
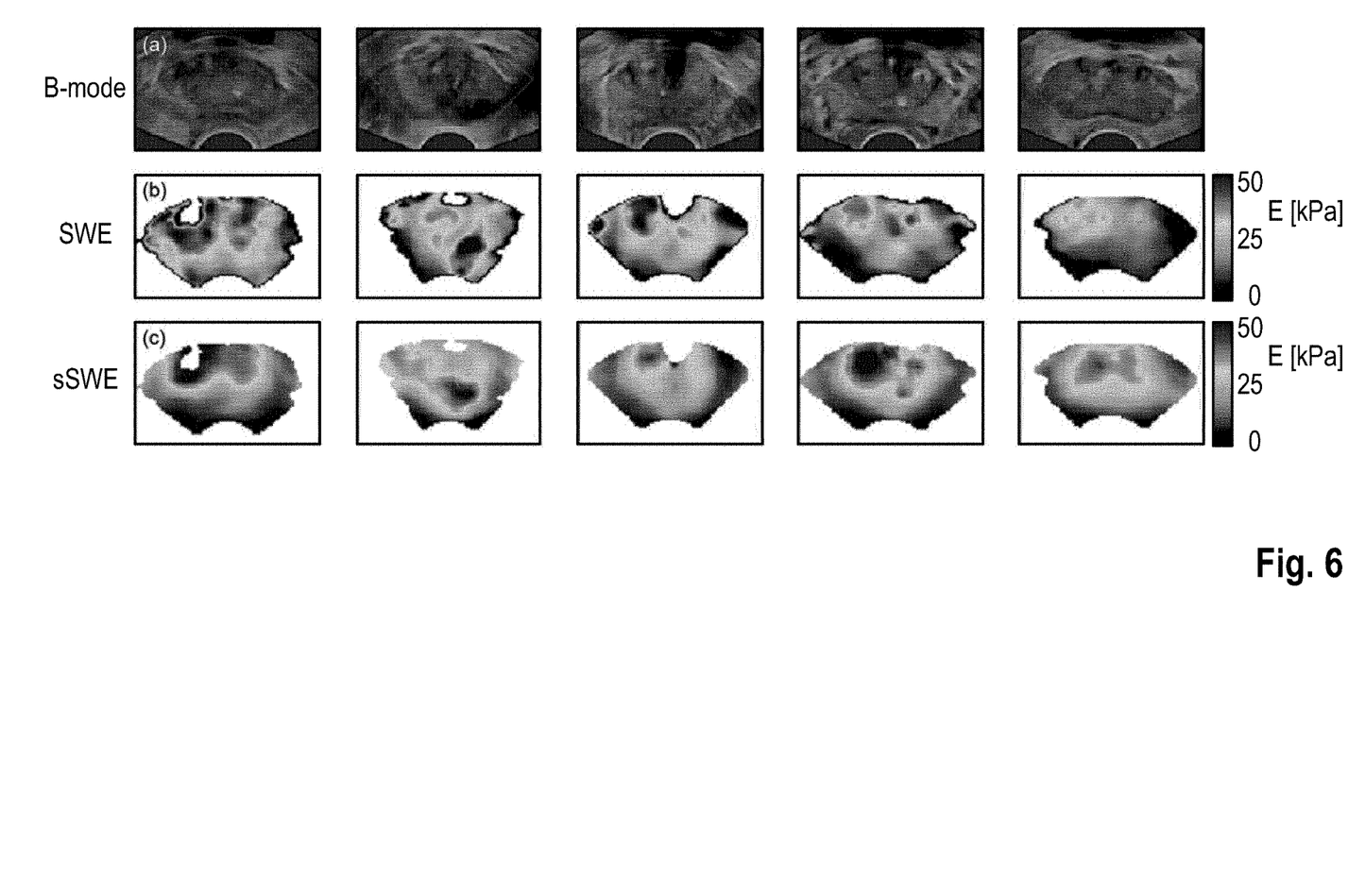
FIG. 6 is an example of B-mode, SWE and sSWE images generated according to an embodiment of the invention.

The results are shown in FIG. 6: It could be shown that the NN was able to accurately map the B-mode images into sSWE images with a pixel-wise mean absolute error of about 4.8 kPa in terms of Young's modulus. Qualitatively, tumour sites characterized by high stiffness were mostly preserved (as validated by histopathology). FIG. 6 show examples from five test patients, wherein the first row (a) depicts the B-mode ultrasound images, the second row (b) depicts the shear-wave elastographic acquisitions, and the third row (c) the corresponding synthetic SWE images obtained by a method according to an embodiment of the invention.

Figure 7:
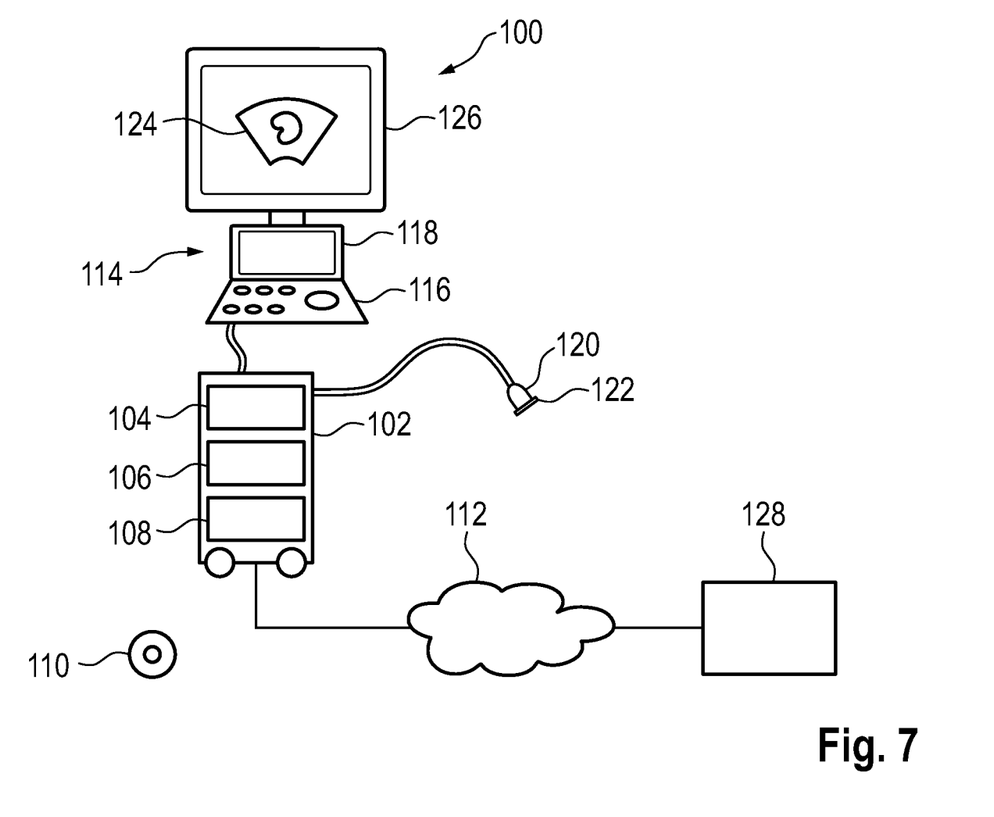
FIG. 7 shows an ultrasound imaging system according to an embodiment of the invention.

FIG. 7 is a schematic representation of an ultrasound system 100 according to an embodiment of the invention and configured to perform the inventive method. The ultrasound system 100 includes a usual ultrasound hardware unit 102, comprising a CPU 104, GPU 106 and digital storage medium 108, for example a hard disc or solid-state disc. A computer program may be loaded into the hardware unit, from CD-ROM 110 or over the internet 112. The hardware unit 102 is connected to a user-interface 114, which comprises a keyboard 116 and optionally a touchpad 118. The touchpad 118 may also act as a display device for displaying imaging parameters. The hardware unit 102 is connected to an ultrasound probe 120, which includes an array of ultrasound transducers 122, which allows the acquisition of B-mode ultrasound images from a subject or patient (not shown), preferably in real-time. B-mode images 124 acquired with the ultrasound probe 120, as well as sSWE images 18 generated by the inventive method performed by the CPU 104 and/or GPU, are displayed on screen 126, which may be any commercially available display unit, e.g. a screen, television set, flat screen, projector etc.

Further, there may be a connection to a remote computer or server 128, for example via the internet 112. The method according to the invention may be performed by CPU 104 or GPU 106 of the hardware unit 102 but may also be performed by a processor of the remote server 128.

The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. A computer-implemented method for generating a synthetic elastography image from a B-mode ultrasound image, the method comprising the steps of
receiving the B-mode ultrasound image of a region of interest at a frame rate;
generating a synthetic elastography image of the region of interest by applying a trained artificial neural network to the B-mode ultrasound image, wherein the generating the synthetic elastography image is at the frame rate,
and further wherein the artificial neural network is trained by a method comprising the steps of:
receiving input training data, namely at least one prior B-mode ultrasound image of a region of interest, wherein the prior B-mode ultrasound image has been acquired at a frame rate during an ultrasound examination of a human or animal subject;
receiving output training data, namely at least one ultrasound elastography image of the region of interest acquired by means of an ultrasound elastography technique during the same ultrasound examination; and
training the artificial neural network to generate the synthetic elastography images by using the input training data and the output training data.

2. The method of claim 1, wherein the input to the trained artificial neural network, namely the B-mode ultrasound image, has the same size and dimensions as the output of the trained artificial neural network, namely the synthetic elastography image.

3. The method of claim 1, wherein the trained artificial neural network comprises at least one convolutional layer, wherein the convolutional layer or layers comprise a filter kernel having a size of 3×3 pixels.

4. The method of claim 1, wherein the trained artificial neural network is a deep fully-convolutional neural network.

5. The method of claim 1, wherein the trained artificial neural network comprises at least one unit comprising two convolutional layers followed by a pooling layer or an up-sampling layer.

6. The method of claim 1, wherein the trained artificial neural network comprises an encoder-decoder architecture, wherein the artificial neural network comprises one encoder part and one decoder part.

7. The method of claim 1, wherein the trained artificial neural network comprises a layer or layers in a deep latent space between the encoder part and the decoder part.

8. The method of claim 7, wherein the trained artificial neural network comprises at least one skip connection from a layer in the encoder part to an equally-sized layer in the decoder part.

9. The method of claim 1, wherein the trained artificial neural network comprises an encoder part comprising a plurality of convolutional layers, wherein each one to three convolutional layers are followed by a pooling layer, and a decoder part comprising a plurality of convolutional layers, wherein each one to three convolutional layers are followed by an up-sampling layer.

10. The method of claim 1, wherein the trained artificial neural network comprises at least one layer including a non-linear activation function such as Leaky ReLUs, ReLUs, hyperbolic tangents, sigmoids, or antirectifiers.

11. The method of claim 1, comprising the further step of applying the trained artificial neural network or a second trained artificial neural network to the B-mode ultrasound image, wherein the output of the trained artificial neural network or the second trained artificial neural network is a confidence map comprising a plurality of confidence scores, each confidence score being representative of the confidence level of the value of a corresponding pixel of the synthetic elastography image.

12. A method for training an artificial neural network or a second artificial neural network for providing a confidence map comprising a plurality of confidence scores, each confidence score being representative of the confidence level of the value of a pixel of a synthetic elastography image, the method comprising the steps of:
receiving input training data comprising at least one synthetic elastography image generated by the method according to claim 1, wherein the B-mode ultrasound image used to generate the synthetic elastography image has been acquired during an ultrasound examination of a human or animal subject;
receiving output training data, namely at least one ultrasound elastography image of the region of interest acquired by means of an ultrasound elastography technique during the same ultrasound examination;
training the artificial neural network by using the input training data and the output training data.

13. A computer program embodied in a non-transitory computer readable medium comprising instruction, which, when the program is executed by a computational unit, causes the computational unit to carry out the method of claim 1.

14. A system for generating a synthetic elastography image from a B-mode ultrasound image, the system comprising:
a first interface, configured for receiving the B-mode ultrasound image of a region of interest at a frame rate;
a computational unit configured for applying a trained artificial neural network to the B-mode ultrasound image to thereby generate a synthetic elastography image of the region of interest at the frame rate;
a second interface, configured for outputting the synthetic elastography image of the region of interest,
wherein the artificial neural network is trained by:
receiving input training data, namely at least one prior B-mode ultrasound image of a region of interest, wherein the prior B-mode ultrasound image has been acquired at a frame rate during an ultrasound examination of a human or animal subject;
receiving output training data, namely at least one ultrasound elastography image of the region of interest acquired by means of an ultrasound elastography technique during the same ultrasound examination; and
training the artificial neural network to generate the synthetic elastography images by using the input training data and the output training data.

* * * * *